(12) United States Patent
Yu

(10) Patent No.: US 8,003,766 B2
(45) Date of Patent: Aug. 23, 2011

(54) MONOCLONAL ANTIBODY SPECIFIC TO OCHRATOXIN A

(75) Inventor: Feng-Yih Yu, Taichung (TW)

(73) Assignee: Chung Shan Medical University, Taichung (TW)

( * ) Notice: Subject to any disclaimer, the term of this patent is extended or adjusted under 35 U.S.C. 154(b) by 31 days.

(21) Appl. No.: 12/425,921

(22) Filed: Apr. 17, 2009

(65) Prior Publication Data

US 2010/0266603 A1  Oct. 21, 2010

(51) Int. Cl.
*C07K 16/00* (2006.01)
*C12P 21/08* (2006.01)

(52) U.S. Cl. ................... 530/388.1; 530/388.5

(58) Field of Classification Search .................. None
See application file for complete search history.

(56) References Cited

OTHER PUBLICATIONS

J. W. Bennett et al., Mycotoxins, Clinical Microbiology Reviews, Jul. 2003, p. 497-516, vol. 16 No. 3.
Annie Pfohl-Leszkowicz et al., Ochratoxin A: An overview on toxicity and carcinogenicity in animals and humans, Mol. Nutr. Food Res., 2007, 51, p. 61-99.
Young-Jin Cho et al., Production of a Monoclonal Antibody against Ochratoxin A and Its Application to Immunochromatographic Assay, Journal of Agricultural and Food Chemistry, 2005, 53 (22), p. 8447-8451.
Miriam M. Ngundi et al., Array Biosensor for Detection of Ochratoxin A in Cereals and Beverages, Analytical Chemistry, 2005, 77 (1), p. 148-154.
Feng-Yih Yu et al., Development of a Sensitive Enzyme-Linked Immunosorbent Assay for the Determination of Ochratoxin A, Journal of Agricultural and Food Chemistry, 2005, 53, p. 6947-6953.
Biing-Hui Liu et al., Development of a Monoclonal Antibody against Ochratoxin A and Its Application in Enzyme-Linked Immunosorbent Assay and Gold Nanoparticle Immunochromatographic Strip, Analytical Chemistry, Sep. 15, 2008, pp. 7029-7035, vol. 80, No. 18.

*Primary Examiner* — Nora Rooney
(74) *Attorney, Agent, or Firm* — WPAT, P.C.; Anthony King

(57) ABSTRACT

This invention provides a monoclonal antibody specific to ochratoxin A and methods of assaying the level of ochratoxin A in food and feed.

10 Claims, 5 Drawing Sheets

FIGURES

SEQUENCE LISTING

<160> NUMBER OF SEQ ID NOS: 4

<210> SEQ ID NO 1
<211> LENGTH: 345
<212> TYPE: DNA
<213> ORGANISM: Mus musculus

<400> SEQUENCE: 1

```
gaattcgccc ttccgtttga tttccagctt ggtcccccct ccgaacgtgt aagctcccta        60
atgtgctgac agtaataggt tgcagcatcc tcctcctcca caggatggat gttgagggtg       120
aagtctgtcc cagacccact gccactgaac ctggcaggga ccccagattc taggttggat       180
acaagataga tgaggagtct gggtggctgt cctggtttct gttggttcca gtgcatataa       240
ctatagccag atgtactgac acttttgctg gccctgtatg agatggtggc cctctgcccc       300
agagatacag ctaaggaagc tggagactgg gtcagcacaa tgtca                      345
```

<210> SEQ ID NO 2
<211> LENGTH: 359
<212> TYPE: DNA
<213> ORGANISM: Mus musculus

<400> SEQUENCE: 2

```
tgaggagacg gtgaccgtgg tcccttggcc ccagtaagca aaccaggcag cccagttatc        60
ctgtcttgca cagtaataaa tggctgtgtc ctcagacttc agactgctca tttgcaggta       120
cagggtggtc ttggcattgt ctctggagat ggtgaatcgg ccttcacag tgtctggata        180 gtaggtgcta ccccaccag tattaatgga tgcgacccac tccagcctct ctccggagt         240 ctggcgaacc aagacatgt catatctact gaaaacgaat ccagaggctg cacaggagag        300
tttcagggac cctccaggct tcactgagcc tcccctgac tcctgcagct gcacctcct         359
```

<210> SEQ ID NO 3
<211> LENGTH: 114
<212> TYPE: PRT
<213> ORGANISM: Mus musculus

<400> SEQUENCE: 3

```
Asp Ile Val Leu Thr Gln Ser Pro Ala Ser Leu Ala Val Ser Leu Gly
  1               5                  10                  15

Gln Arg Ala Thr Ile Ser Tyr Arg Ala Ser Lys Ser Val Ser Thr Ser
             20                  25                  30

Gly Tyr Ser Tyr Met His Trp Asn Gln Gln Lys Pro Gly Gln Pro Pro
         35                  40                  45

Arg Leu Leu Ile Tyr Leu Val Ser Asn Leu Glu Ser Gly Val Pro Ala
     50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ile Arg
                 85                  90                  95

Glu Leu Thr Arg Ser Glu Gly Gly Pro Ser Trp Lys Ser Asn Gly Arg
            100                 105                 110

Ala Asn
```

<210> SEQ ID NO 4
<211> LENGTH: 119
<212> TYPE: PRT
<213> ORGANISM: Mus musculus

<400> SEQUENCE: 4

```
Glu Val Gln Leu Gln Glu Ser Gly Gly Gly Ser Val Lys Pro Gly Gly
  1               5                  10                  15

Ser Leu Lys Leu Ser Cys Ala Ala Ser Gly Phe Val Phe Ser Arg Tyr
             20                  25                  30
```

-continued

```
Asp Met Ser Trp Val Arg Gln Thr Pro Glu Lys Arg Leu Glu Trp Val
        35                  40                  45

Ala Ser Ile Asn Thr Gly Gly Gly Ser Thr Tyr Tyr Pro Asp Thr Val
    50              55                      60

Lys Gly Arg Phe Thr Ile Ser Arg Asp Asn Ala Lys Thr Thr Leu Tyr
65              70                  75                      80

Leu Gln Met Ser Ser Leu Lys Ser Glu Asp Thr Ala Ile Tyr Tyr Cys
            85                  90                  95

Ala Arg Gln Asp Asn Trp Ala Ala Trp Phe Ala Tyr Trp Gly Gln Gly
            100             105                 110

Thr Thr Val Thr Val Ser Ser
        115
```

MONOCLONAL ANTIBODY SPECIFIC TO OCHRATOXIN A

FIELD OF THE INVENTION

This invention provides a monoclonal antibody specific to ochratoxin A and methods of assaying the level of ochratoxin A in food and feed.

DESCRIPTION OF PRIOR ART

Ochratoxin A (OTA) is a naturally occurring mycotoxin produced primarily by *Aspergillus ochraceus* and *Penicillium verrucosum*. It is mainly found as a contaminant of cereals, cereal products, and coffee beans. Toxicological studies indicate that OTA is generally absorbed from the gastrointestinal tract in animals and shows strong toxic effects in their livers and kidneys. Several studies have revealed that OTA was the major causative factor in mycotoxic porcine nephropathy and Balkan endemic nephropathy in many European countries (Bennett et al., *Clinic. Microbiol. Rev.* 2003, 16, 497-516 & Pfohl-Leszkowicz *Mol. Nutr. food. Rev.* 2007, 51, 61-99).

In addition, the toxin is also considered to be teratogenic, mutagenic, and immunosuppressive in certain animal models. Since consumption of food contaminated with OTA is associated with an increased incidence of upper urinary tract tumors in humans, the International Agency for Research on Cancer (IARC) has classified OTA as a possible human carcinogen (group 2B). To protect human and animal exposure to OTA, the European Union enacted a regulatory limit for the levels of OTA in cereals (5 µg/kg), roasted coffee (5 µg/kg), and instant coffee (10 µg/kg).

In order to determine the OTA levels in foods and feeds, several research efforts have been conducted to develop sensitive and specific methods for OTA detection. Currently high-performance liquid chromatography (HPLC)—fluorescence detection with good accuracy and reproducibility is the most widely employed method for monitoring OTA. However, HPLC requires the involvement of highly qualified personnel and extensive sample cleanup as well as expensive equipment. Development of immunochemical analysis has led to many rapid and sensitive methods for monitoring and quantifying OTA in contaminated food. Several groups have established immunoassays for OTA (Ngumdi et al., *Anal. Chem.* 2005, 77, 148-154), but most of the HPLC and enzyme-linked immunosorbent assay (ELISA), are not suitable for on-site detection because of the long incubation time, tedious washing steps, and the application of instrumentation.

SUMMARY OF THE INVENTION

The invention provides a monoclonal antibody for binding ochratoxin A consisting of a heavy chain polypeptide having the sequence of SEQ ID NO: 4 and a light chain polypeptide having the sequence of SEQ ID NO: 3.

DETAILED DESCRIPTION OF THE INVENTION

This invention provides a monoclonal antibody for binding ochratoxin A consisting of a heavy chain polypeptide having the sequence of SEQ ID NO: 4 and a light chain polypeptide having the sequence of SEQ ID NO: 3. The antibody is loaded on a pharmaceutically acceptable carrier and is immobilized on an insoluble matrix.

The monoclonal antibody mentioned above is used to prepare a composition conjugated to a detectable label for enzyme immunoassay or immuno-chromatographic strip assay.

The monoclonal antibody of Ochratoxin A is produced from cell line 9C9H9, and can be conjugated to a detectable label for enzyme immunoassay or immuno-chromatographic strip assay. The enzyme immunoassay or immuno-chromatographic strip assay is applied to detect the level of ochratoxin A in a subject. The detecting assay further comprises an amount of ochratoxin A conjugated to an enzyme to compete with any ochratoxin A in a subject to form complexes with said antibody. In a preferred embodiment, the subject here includes but is not limited to coffee and feed. The feed aforementioned comprises forage and grains.

The monoclonal antibody can also be conjugated with gold-nanoparticles which have been used in biosensors or immunochromatographic strips for the detection of ochratoxin A.

Example

Example 1

Preparation of Ochratoxin and Other Chemicals

Figure 1:
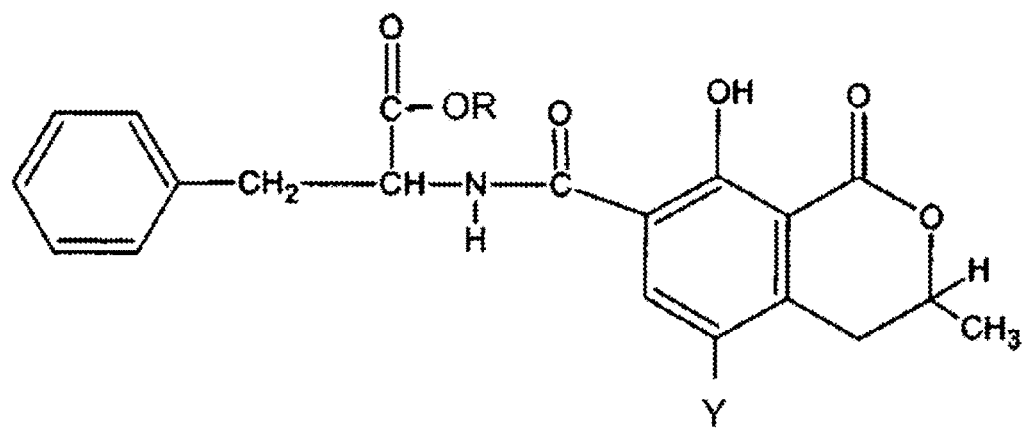
FIG. 1. Structures of ochratoxin A (OTA), ochratoxin B (OTB), and ochratoxin C (OTC).

OTA and ochratoxin B (OTB) (FIG. 1) were purchased from Sigma Chemical Co. (St. Louis, Mo.). A standard solution of OTA at 20 µg/mL in toluene acetic acid (99:1) was prepared and assayed according to the AOAC method. Ochratoxin toxin C (OTC) (FIG. 1) was prepared by esterification of OTA according to previous method (Yu, F. Y. et. al., *J. Agric. Food. Chem.* 2005, 53, 6947-6953).

Bovine serum albumin (BSA), γ-globulin, gelatin, ovalbumin (OVA), ammonium biocarbonate, Tween 20, dimethyl sulfoxide, 1,1-carbonyldiimidazole (CDI), 1-ethyl-3-(3-dimethylaminopropyl)-carbodimide (EDC), and N-hydroxysuccinimide were obtained from Sigma Chemical Co. Goat antimouse peroxidase conjugate and keyhole limpet hemocyanin (KLH) were obtained from Pierce Chemical Co. (Rockford, Ill.). Horseradish peroxidase (HRP) was obtained from Boehringer Mannheim Biochemicals (Indianapolis, Ind.). HRP substrate solution 3,3,5,5-tetramethylbenzidine (TMB) was obtained from Neogen Corp. (Lexington, Ky.).

Ammonium sulfate, absolute ethanol, HPLC grade acetonitrile, and methanol were obtained from Merck (Darmstadt, Germany). Microtiter plates and strips (low and high protein binding) were obtained from Nunc (Roskilde, Denmark). An ELx 50 ELISA washer was purchased from Bio-Tek instruments (Winooski, Vt.). A Vmax automatic ELISA reader was purchased from Molecular Devices Co. (Menlo Park, Calif.). Polyethylene glycol (PEG) 1500, hypoxanthine (H), aminopterin (A), and thymidine (T) were purchased from Boehringer Mannheim Biochemicals (Indianapolis, Ind.). Freund's incomplete adjuvant, Dulbeco Modified Eagle's Medium (DMEM), fetal calf serum, and penicillin-streptomycin were obtained from GIBCO Laboratories (Grand Island, N.Y.).

A mouse mAb isotyping kit was obtained from Boehringer Mannheim (Indianapolis, Ind.). Virus-free, 9-10-week-old, female BALB/c mice were obtained from National Animal Research Center (Taipei, Taiwan). The murine myeloma cell line P3/NS-1/1-AG4-1 (NS-1) was obtained from Bio-resources Collection and Research Center in Taiwan. Gold nanoparticle (10 and 40 nm in diameter) was obtained from BBInternational (Cardiff, U.K.). A Easypack Developer's Kit consisted of three pads (sample, conjugate release, and absorbent pads) and one nitrocellulose membrane plate was purchased from MDI Membrane Technologies (Ambala, India). The 0.45-μm syringe filter was obtained from Gelman Science (Ann Arbor, Mich.). All other chemicals and organic solvents used were of reagent grade or better.

Example 2

Preparation of Various Ota (Ochratoxin A) Conjugate

First conjugate OTA to KLH (keyhole limpet hemocyanin). OTA was conjugated to KLH in the presence of EDC under the following conditions. The EDC solution (1.0 mg of EDC in 0.02 mL of double-distilled $H_2O$) was freshly prepared and then added to an OTA solution (1.0 mg of OTA in 0.4 mL of 25% ethanol). The mixture was added slowly to 2.0 mg of KLH, which was dissolved in 0.4 mL of conjugation buffer (0.1 M 2-N morpholinoethanesulfonic acid, 0.9 M NaCl, pH 4.7) and kept at room temperature for 2 hours. After reaction, the mixture was dialyzed against 2 L of 0.01 M phosphate buffer containing 0.15 M NaCl (PBS, pH 7.5) for 72 hours with two exchanges of PBS and then lyophilized for storage at −20° C.

OTA was conjugated to OVA by the water-soluble carbodiimide method and used as a solid-phase antigen for the indirect competitive ELISA. In a typical reaction, 0.5 mg of OTA in 0.2 mL of conjugation buffer was mixed with 2.5 mg of OVA first, and then 1 mg of EDC was added to the mixture with constant stirring. After the coupling reaction was carried out at 25° C. for 2 hours, the mixture was dialyzed against PBS for 72 hours and then lyophilized for storage.

Conjugation of OTA to HRP (Horseradish peroxidase) was achieved by the CDI method Briefly, 0.2 mg of OTA in 0.05 mL of acetone was mixed with 0.4 mg of CDI, and then a HRP solution (0.8 mg of HRP in 0.3 mL of 0.1 M, pH 9.6, carbonate buffer) was added. After being stirred at room temperature for 2 hours, the mixture was dialyzed against PBS for 72 hours and then lyophilized.

Example 3

Production of Monoclonal Antibody

First step was Immunization. For generating mAbs specific to OTA, four female BALB/c mice (9-10 weeks of age) were each immunized with 40 μg of OTA-KLH in PBS that had been emulsified with an equal volume of Freund's complete adjuvant. Four weeks after the initial intraperitoneal immunization, weekly booster injections were made with the same amount of immunogen in PBS containing no adjuvant. Blood samples were collected from the tail of each mouse at weekly intervals after each booster injection. A competitive indirect (ci) ELISA as described below was used to determine the antibody specificity in the serum.

The mouse with the highest antibody specificity (10 weeks after the initial immunization, including three booster injections) was selected for fusion reaction. Four days before fusion, the mouse was primed with a total of 50 μg of immunogen. The mouse was euthanized 3 days after the final immunization, and the entire spleen was aseptically removed and mashed with a glass pestle. The spleen cells were then passed through a cell dissociation sieve-tissue grinder kit packed with mesh 80 (CD-1, Sigma) to produce a single-cell suspension, which was then mixed with $1 \times 10^7$ myeloma cells.

The cells was centrifuged, suspended in 0.2 mL of HT medium, and then fused by gradually adding 1 mL of PEG 1500 in 1 min into the cell pellet. HT medium was used to do slow dilution of PEG. The cell pellet was rotated for further 1 min, then 1 mL of medium added over 1 min, 2 mL medium over 2 min, wait 2 min, and then 4 mL of medium over 1 min and wait 4 min. Finally, 8 mL was added over 1 min. After centrifugation at 1500 g for 10 min, the cells were pelleted again, resuspended in hypoxanthine, aminopterin, and thymidine (HAT) medium plus normal mouse erythrocytes to a final concentration of 0.5%, and plated into 96-well tissue culture plates.

The colonies were fed every fifth day with freshly prepared HAT medium. When the colonies reached at least half-confluence in the well, hybridomas were screened for specific antibodies specific to OTA using a ciELISA described later. Two hybridoma cell lines from the mouse immunized with OTA-KLH were obtained. Wells containing positive cells were cloned by the limiting dilution method into 96-well tissue culture plates.

After spleen/NS-1 cell fusion and cloning, the ciELISA with OTA-OVA as a coated reagent was used for screening the hybridoma cells, which were able to produce mAbs specific to OTA. Of the 630 wells examined, only two clones gave strong positive signals in the ciELISA; among them, the clone, 9C9, showed the highest affinity for OTA. Therefore, the supernatant of 9C9 culture was aspirated from the fusion well and subjected to limiting dilution for hybridoma selection. After limiting dilution and ELISA screening, clone 9C9H9 showing the highest affinity to OTA was selected for production of culture supernatant and ascites fluid.

Example 4

Production of Ascites Fluid

Female BALB/c mice, 10 weeks old, were injected intraperitoneally with 0.5 mL of pristane 7 days before receiving an intraperitoneal injection of $2 \times 10^6$ hybridoma cells suspended in DMEM. Ascites fluid developed 2 to 3 weeks after the injection of the cells and was collected every other day for 6 days. The ascites fluid was centrifuged at 7000 rpm (5900 g) for 5 min to remove cell debris. The IgG from the cleared ascites fluid was purified by ammonium sulfate precipitation (50% saturation for the final solution) twice and then stored at −70° C.

Example 5

Characterization of Monoclonal Antibodies

A mouse mAb isotyping kit made by Roche was used to determine the isotypes of mAb. The isotype of mAb produced by cell line 9C9H9 was found to be immunoglobulin G1, κ-light chain.

The mRNAs extracted from 9C9H9 cell were transferred into cDNA and rendered for sequence analysis. The results of light chain and heavy chain DNA sequences were shown in sequence listing SEQ ID NOS: 1 and 2. The cDNA sequences were further turned into amino acid sequences SEQ ID NOS: 3 and 4.

Both the cdELISA (direct competitive ELISA) and ciELISA (indirect competitive ELISA) were used to determine the specificity of 9C9H9 mAb.

Indirect Competitive ELISA was than used to characterize each mAb. Briefly, each well of a microtiter plate was coated with 0.1 mL of the OTA-OVA and kept at 4° C. overnight. After the plate had been washed four times with Tween-PBS (0.35 mL/well; 0.05% Tween 20 in PBS) using an automated ELISA washer, 0.17 mL of gelatin-PBS (0.17 mL/well; 0.1% gelatin in PBS) was added and allowed to incubate at 37° C. for 30 min. The plate was washed again and 0.05 mL of OTA standard with concentrations from 0.01 to 100 ng/mL or extracted samples (0.05 mL/well in PBS) were added to each well, and then the anti-OTA mAb (25 ng/mL in PBS, 0.05 mL/well) was added to all wells and incubated at 37° C. for 50 min. After incubation, the plate was washed four times with Tween-PBS, and 0.1 mL of goat antimouse IgG-HRP conjugate (1:20000 dilution) was added and incubated at 37° C. for 45 min. The plate was washed four times with Tween-PBS, and 0.1 mL of TMB substrate solution was added. After 10 min of incubation at room temperature, 0.1 mL of 1 N hydrochloric acid was added to stop the reaction. Absorbance at 450 nm was determined in a Vmax automatic ELISA reader.

Another ELISA method (direct competitive ELISA) was used to characterize mAb. The rabbit anti-mouse-Fc antibody was diluted in PBS (2 μg/mL), and 0.1 mL of the diluted form was coated onto each well. After incubation at 37° C. for 1 h and washing with Tween-PBS. The anti-OTA mAb supernatant was diluted in PBS (5 μg/mL) and 0.1 mL of the diluted form was used to coat each well. After the plate had been incubated at 4° C. overnight, it was washed with Tween-PBS followed by blocking with gelatin-PBS at 37° C. for 30 min. The plate was washed again with Tween-PBS four times, and then OTA standard (0.05 mL/well in PBS) concentrations from 0.01 to 100 ng/mL or samples together with the OTA-HRP conjugate (30 ng/mL, in PBS, 0.05 mL/well) were added and incubated at 37° C. for 50 min. The plate was washed four times with PBS-Tween, and 0.1 mL of TMB substrate solution was added. After incubation at room temperature in the dark for 10 min, the reaction was terminated by adding 0.1 mL of 1 N HCl. The absorbance at 450 nm was determined in the Vmax automatic ELISA reader.

Figure 2:
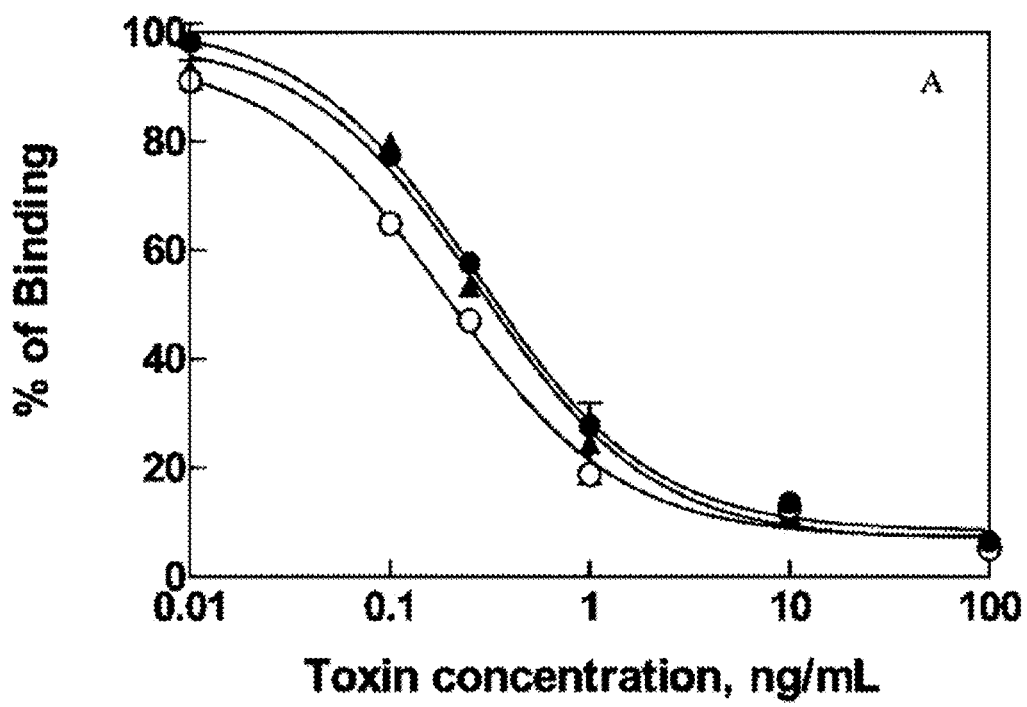
FIG. 2. (A) Cross-reactivity of anti-OTA antibodies with OTA (●), OTB (○), and OTC (▲) in a cdELISA (direct competitive ELISA). (B) Cross-reactivity of anti-OTA antibodies with OTA (●), OTB (○), and OTC (▲) as determined by a ciELISA (indirect competitive ELISA).
Figure 2:
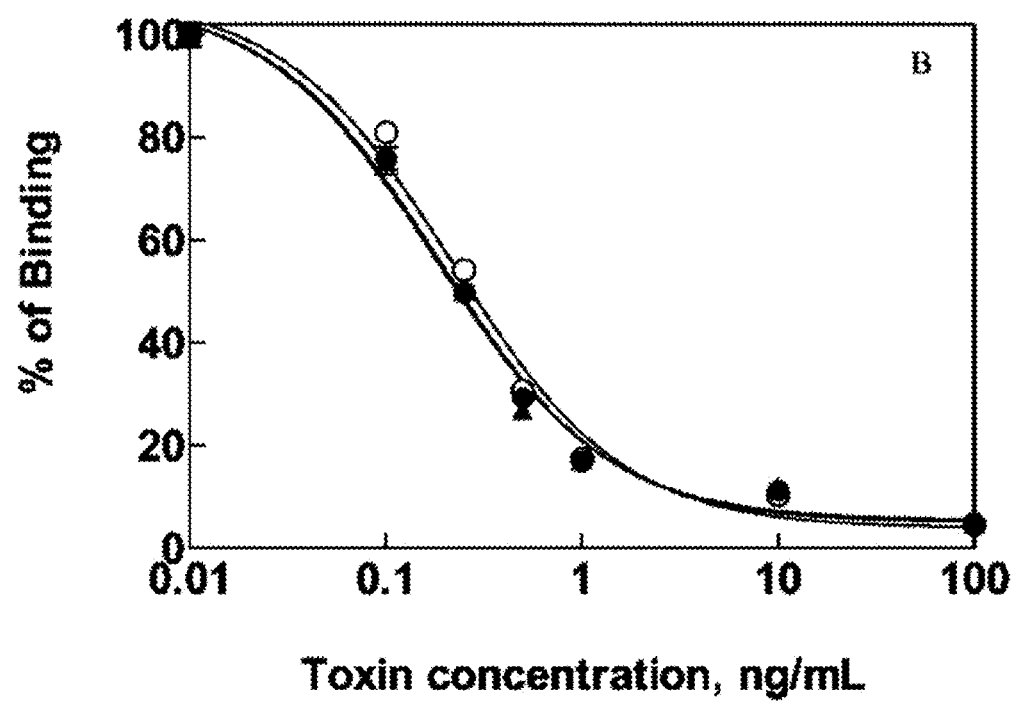

As shown in FIG. 2A, in cdELISA experiment the concentrations causing 50% inhibition (IC50) binding of mAb to OTA-OVA by free OTA, OTB, and OTC were found to be 0.32, 0.17, and 0.28 ng/mL. A similar result was found in the ciELISA, in which OTA-OVA were coated onto the wells of ELISA plates to serve as solid-phase antigen. The IC50 of binding of mAb to OTA-OVA by free OTA, OTB, and OTC were calculated to be 0.28, 0.35, and 0.25 ng/mL, respectively. (FIG. 2B)

However, phenylalanine and citrinin, two molecules with chemical structures similar to a part of OTA molecule, did not inhibit the binding of mAb to the marker antigen (OTA-HRP or OTA-OVA) in either ELISA system even at a concentration as high as 100 μg/mL.

Example 6

Analysis of OTA in Coffee Samples with mAb-Based cdELISA Fifteen coffee samples were collected from local food stores and subjected to cdELISA to determine the contaminated levels of OTA. Briefly, each sample (10 g) was homogenized with 100 mL of extraction solvent (methanol/water, 50/50, v/v) for 5 min. After centrifugation at 10 000 rpm (14000 g) for 10 min, the extraction solution was passed through a 0.45-μm syringe filter. One milliliter of the supernatant solution was aspirated, diluted with 4 mL of PBS, and directly subjected to cdELISA. For on-site immunochromatographic strip assay, the extraction coffee pellet was precipitated at room temperature for 5 minutes. The clear solution was aspirated and diluted for the strip test.

The results were presented in Table 1. Eleven of the 15 examined samples were found to be ochratoxins-positive in the detection system. Among them, the extract of sample 3 showed the highest ochratoxin level at 10.97 ng/mL (54.85 ng/g) and samples 14 and 15 also had ochratoxin levels higher than 1.0 ng/mL. The remaining eight positive samples were lower than 1.0 ng/mL.

TABLE 1

ELISA and Immunochroatographic Strip Analysis of OTA in Coffee Samples

| samples | ELISA ng/mL ± SD | ELISA ng/g ± SD[b] | immunochromatographic strip[a] |
|---|---|---|---|
| green coffee beans | | | |
| 1 | not detected | not detected | − |
| 2 | not detected | not detected | − |
| 3 | 10.97 ± 0.27 | 54.85 ± 1.35 | + |
| 4 | not detected | not detected | − |
| 5 | not detected | not detected | − |
| roasted coffee beans | | | |
| 6 | 0.46 ± 0.03 | 2.30 ± 0.15 | − |
| 7 | 0.41 ± 0.04 | 2.05 ± 0.20 | − |
| 8 | 0.87 ± 0.09 | 4.35 ± 0.45 | − |
| 9 | 0.6 ± 0.04 | 3.0 ± 0.2 | − |
| 10 | 0.72 ± 0.03 | 3.6 ± 0.15 | − |
| instant coffee | | | |
| 11 | 0.6 ± 0.04 | 3.0 ± 0.20 | − |
| 12 | 0.77 ± 0.15 | 3.83 ± 0.75 | − |
| 13 | 0.86 ± 0.12 | 4.3 ± 0.6 | − |
| 14 | 1.19 ± 0.08 | 5.93 ± 0.40 | − |
| 15 | 1.36 ± 0.2 | 6.8 ± 1.0 | − |

[a]Each sample was extracted twice and each extract was analyzed in duplicate.
[b]One micro liter of extract solution contains 0.2 g of coffee samples.

Example 7

Preparation of Antibody-Gold Nanoparticle Probe

OTA mAbs were dialyzed against boric acid-borax buffer for 24 hours at 4° C. and then centrifuged at 10,000 rpm (14000 g) for 10 minutes to get a clear supernatant for conjugation. The pH of the gold nanoparticle (40 or 10 nm in diameter) solution was adjusted to pH 9.0 with 0.1 M $K_2CO_3$ (pH 11.5) for conjugation with OTA mAb. The 50 μg of anti-OTA mAb was added dropwise to the 10 mL of pH-adjusted gold nanoparticle solution with gentle stirring. The mixture was reacted for 1 hour at room temperature and blocked by 10% (w/v) filtered BSA for 30 minutes. This mixture was centrifuged at 14,000 rpm (19000 g) for 30 minutes at 4° C., and then the supernatant was discarded; the gold pellets were resuspended by adding 450 μL of 20 mM Tris-buffered saline (pH 8.0) with 1% BSA and 0.1% sodium azide. This antibody-gold nanoparticle probes were stored at 4° C. until use.

Example 8

Preparation of Immunochromatographic Strip

An immunochromatographic strip consisted of three pads (sample, conjugate release, and absorbent pads) and one nitrocellulose membrane with test and control zones. The test and control zones of the nitrocellulose membrane were manually pipetted with 1 μL of OTA-OVA (0.8 mg/mL) conjugate and 0.5 μL of rabbit anti-mouse IgG antibody (1 mg/mL), respectively. The treated nitrocellulose membrane was dried for 10 min at room temperature. The OTA mAb-gold nanoparticle conjugate (5 μL/strip) was added to an untreated glass-fiber membrane to be used as a conjugate release pad. The conjugate pad was air-dried for 5 min. The release pad was pasted on the plate by overcrossing 4 mm with the NC membrane. The sample pad was also pasted on it by overcrossing 6 mm with release pad. The absorbent pad was pasted on the top of the membrane sheet. The whole assembled sheet was cut lengthways with a automatic cutter and divided into strips (5 mm×75 mm).

Monoclonal antibody was applied to construct an effective immunochromatographic strip, in which the OTA-OVA conjugate competes with OTA in the sample solution for the antibody-gold nanoparticle label. A schematic description of the immunochromatographic strip test format was shown in FIG. 3. In the absence of OTA in the sample solution, the antibody-gold nanoparticle conjugate was bound and trapped by the OTA-OVA conjugate to form a visible spot on the test zone. In contrast, if sufficient concentration of OTA was present in the sample solution, the toxin would occupy the antigen binding sites on the antibody-gold nanoparticle conjugates; consequently, the limited antibody-gold nanoparticle conjugates failed to bind with the OTA-OVA conjugate on the test zone.

Figure 3:
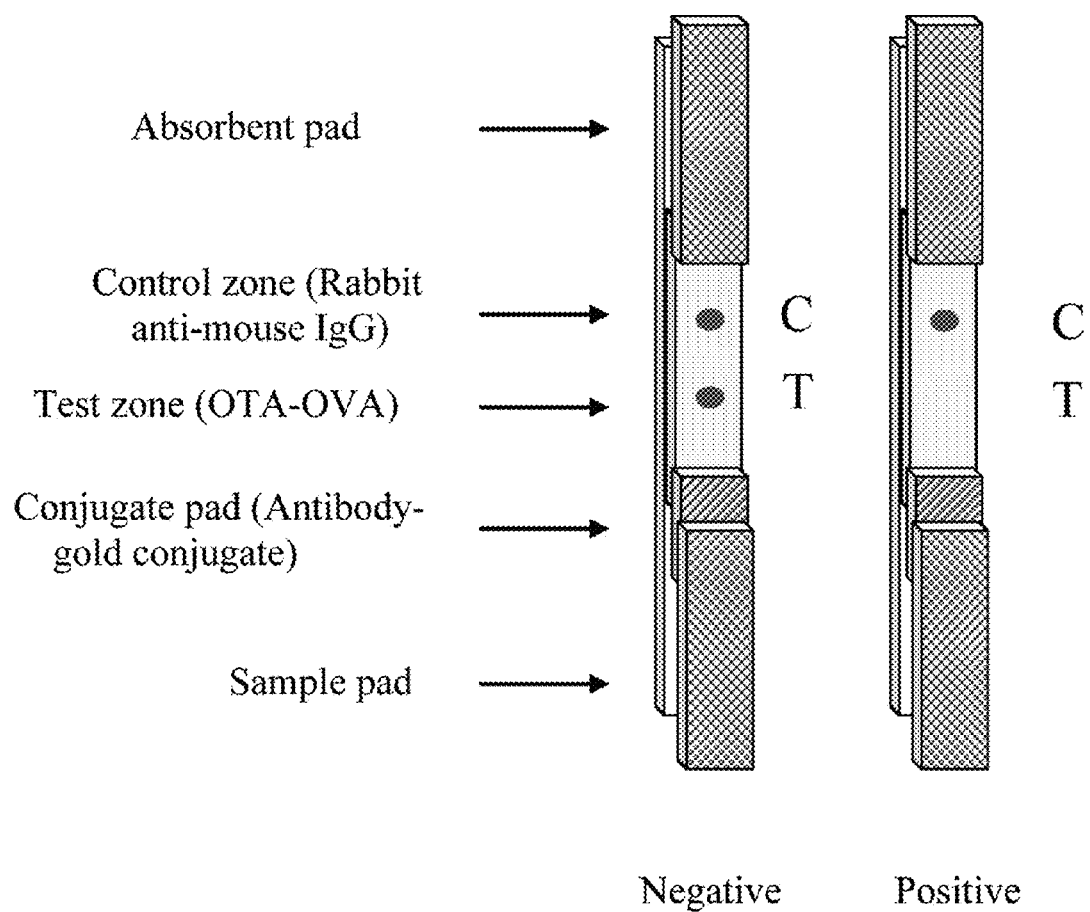
FIG. 3. Schematic illustration of immunochromatographic strip: C, control zone (rabbit anti-mouse IgG); T, test zone (OTA-OVA).

The absence of color spot on the test zone indicated a positive result (FIG. 3). Control zone coated with rabbit anti-mouse secondary antibody was constructed to verify whether the assay has been performed properly; this control zone should always show a red color spot under an accurate operation regardless of the presence or absence of OTA. An OTA-free sample shows two red spots, whereas a positive sample with OTA presents only one red spot on the membrane.

Example 9

Characterization of OTA Immunochromatographic Strip

The immunochromatographic strip that was based on the use of colored gold nanoparticle antibody conjugates as detector reagents was an emerging format for immunoassay for mycotoxins. The principle of the immunochromatographic strip relies on the migration of test samples and antibody-gold nanoparticle conjugates along membrane strips on which the binding interactions take place. The results of an immunochromatographic strip could be examined visually, thus providing fast and simple on-site detection in less than 10 min without the need of skilled personnel and any instruments. Since coffee samples collected from different regions has been reported to be contaminated with various amounts of OTA, an effective on-site detection of OTA in coffee samples was needed. There had been first reported an immunochromatographic strip for OTA analysis with a detection limit in the range of 500 ng/mL, which was not sensitive enough to be practically applied in sample analysis according EU regulatory procedures (Cho, Y. J. et al., *J. Agric. Food. Chem.* 2005, 53, 8447-8451). In the present study, a mAb specific to OTA was generated, and then a sensitive competitive direct (cd) ELISA and a monoclonal antibody (mAb)-based gold nanoparticle immunochromatographic strip were established for such purposes.

Figure 4:
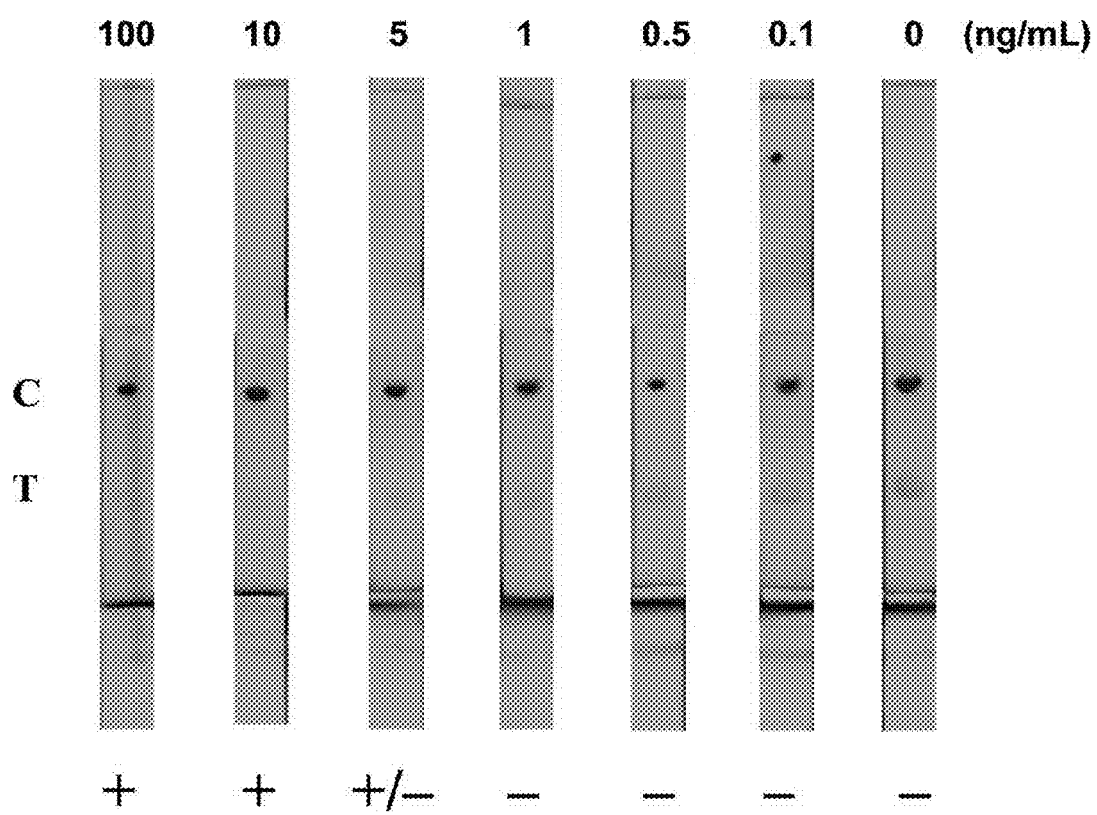
FIG. 4. Represent limitation of OTA detection with immunochromatographic strip. A series of dilutions (0-100 ng/mL) of standard OTA was dissolved in PBS. A concentration higher than 5 ng/mL OTA was found to cause a disappearance of red spot at the test zone.

Various concentrations of OTA standard solution (0-100 ng/mL) were subjected to an immunochromatographic strip test. The whole assay could be completed in less 10 min, and the detection limit of the immunochromatographic strip test for OTA was 5 ng/mL (FIG. 4). In order to characterize and define the cutoff level for each selected concentration, more than n=10 measurements were tested in our immunochromatographic strip detection system. OTA at a concentration above 5 ng/mL occupied all the antibody-gold nanoparticle conjugates and prevented the antibody-gold nanoparticle conjugates from binding with the OTA-OVA on the test zone, but the antibody-gold nanoparticle conjugates captured by the rabbit anti-mouse antibody on the membrane resulted in only one spot on the control zone.

Example 10

Assay of OTA in Coffee Samples with Immunochromatographic Strip

Three hundred microliters of diluted extraction sample solutions and the different concentrations of OTA standard solution (0-100 ng/mL) were added per well. Subsequently, one immunochromatographic strip was dipped into each well vertically. The extracted samples or OTA standard solution was migrated up the membrane. The strip test was allowed to developed color for 10 min, and test results were determined visually.

Figure 5:
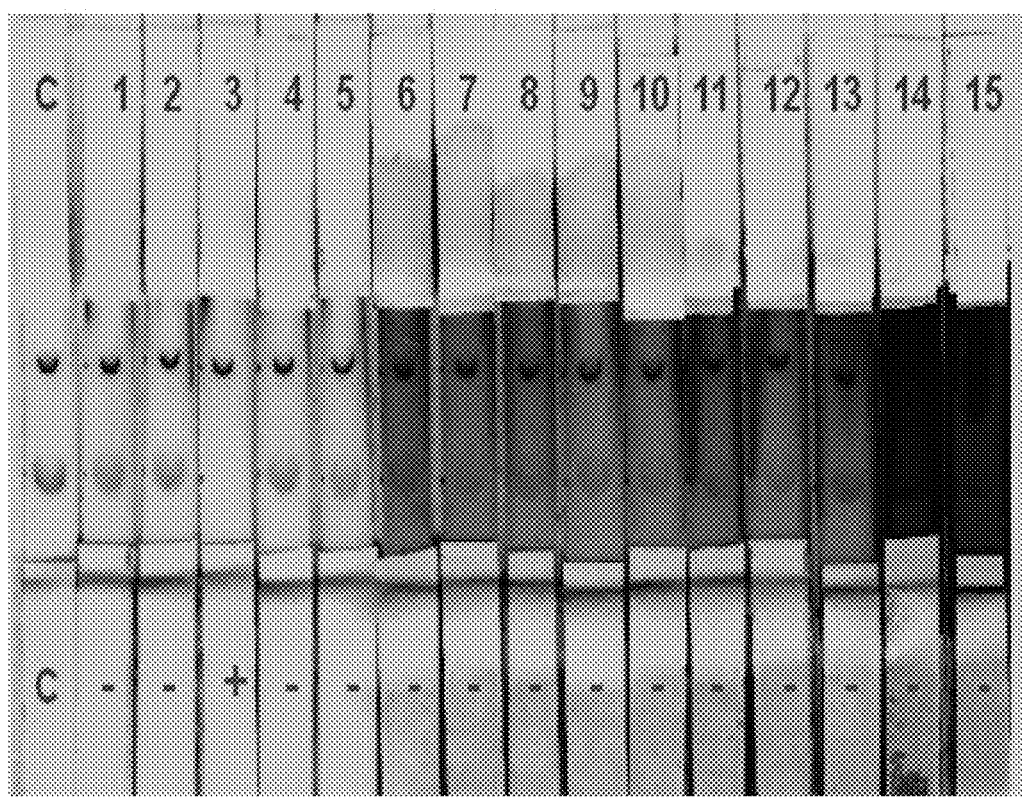
FIG. 5. Represent Detection of OTA with immunochromatographic strip in control and 15 coffee samples. Control strip containing no OTA shows two red spots on the membrane. Sample 3, which contains more than 10 ng/mL ochratoxins, is found to cause a disappearance of red spot at the test zone.

Results were shown in Table 1. Sample 3 containing 10.97 ng/mL ochratoxins in ELISA gave a positive result with only one spot on the strip membrane (FIG. 5). All the remaining coffee samples with toxin levels lower than 5.0 ng/mL demonstrated two red spots on the membrane, indicating that they were negative in our immunochromatographic strip assay.

What is claimed is:

1. A monoclonal antibody for binding ochratoxin A consisting of a heavy chain polypeptide having the sequence of SEQ ID NO: 4 and a light chain polypeptide having the sequence of SEQ ID NO: 3.

2. The monoclonal antibody of claim 1, wherein the antibody is immobilized on an insoluble matrix.

3. The monoclonal antibody of claim 1, wherein the antibody is added to a glass-fiber membrane.

4. The monoclonal antibody of claim 1, which is used to prepare a composition comprising the monoclonal antibody of claim 1 conjugated to a detectable label for enzyme immunoassay or immuno-chromatographic strip assay.

5. The monoclonal antibody of claim 4, wherein said enzyme immunoassay or immuno-chromatographic strip assay is applied to detect the level of ochratoxin A in a sample.

6. The monoclonal antibody of claim 4, which is bound to a solid phase.

7. The monoclonal antibody of claim 4, wherein said enzyme immunoassay or immune-chromatographic strip assay comprises an amount of ochratoxin A conjugated to an enzyme or protein to compete with any ochratoxin A in a subject to form complexes with said antibody.

8. The monoclonal antibody of claim 4, wherein the immuno-chromatographic strip assay further comprises a gold nanoparticle attached to the monoclonal antibody.

9. The monoclonal antibody of claim 5, wherein the sample is coffee or feed.

10. The monoclonal antibody of claim 9, wherein the feed comprises forage and grains.

* * * * *